United States Patent [19]

Katsuyama et al.

[11] Patent Number: 4,897,347
[45] Date of Patent: Jan. 30, 1990

[54] MULTILAYER ANALYSIS FILM FOR ANALYZING TRANSAMINASE

[75] Inventors: Harumi Katsuyama; Toshikazu Amano, both of Saitama, Japan

[73] Assignee: Fuji Photo Film Co., Ltd., Kanagawa, Japan

[21] Appl. No.: 773,911

[22] Filed: Sep. 9, 1985

Related U.S. Application Data

[63] Continuation-in-part of Ser. No. 389,345, Jun. 17, 1982, abandoned.

[30] Foreign Application Priority Data

Jun. 17, 1981 [JP] Japan .................................. 56-93632

[51] Int. Cl.$^4$ .......................... C12Q 1/52; C12Q 1/26; C12Q 1/28
[52] U.S. Cl. ........................................ 435/16; 435/25; 435/28; 435/805; 422/56; 422/57
[58] Field of Search ................ 435/4, 16, 25, 28, 190, 435/193, 805, 16; 422/56, 57

[56] References Cited

U.S. PATENT DOCUMENTS

| | | | |
|---|---|---|---|
| 4,166,763 | 9/1979 | Esders et al. | 435/25 |
| 4,246,342 | 1/1981 | Misaki et al. | 435/16 |
| 4,292,272 | 9/1981 | Kitajima et al. | 422/57 |
| 4,452,887 | 6/1984 | Kitajima et al. | 435/805 |
| 4,503,145 | 3/1985 | Katsuyama et al. | 435/805 |

Primary Examiner—Esther M. Kepplinger
Attorney, Agent, or Firm—Sughrue, Mion, Zinn, Macpeak & Seas

[57] ABSTRACT

A multilayer analysis film for assaying transaminase in a coupled reaction system by a kinetic method comprises (1) a porous layer containing a transaminase substrate, (2) a coloring indicator layer for the detection of hydrogen peroxide, and (3) a transparent support, integrally laminated in this order. Pyruvate oxidase is located in a large excess in the uppermost porous layer where a rate-determining step receives maximum exposure to oxygen in the air. By the use of the analysis film, transaminase activity can be assayed with high sensitivity.

15 Claims, 2 Drawing Sheets

MULTILAYER ANALYSIS FILM FOR ANALYZING TRANSAMINASE

CROSS-REFERENCE TO RELATED APPLICATION

This application is a continuation-in-part of U.S. Application Ser. No. 389,345, filed June 17, 1982, entitled "MULTILAYER ANALYSIS FILM FOR ANALYZING TRANSAMINASE", by Katsuyama et al, now abandoned.

BACKGROUND OF THE INVENTION

1. Field of the Invention

This invention relates to an improved multilayer analysis film suitable for highly sensitive, quantitative analysis of transaminase activity.

2. Development of the Invention

Various transaminases are known as enzymes capable of transferring an amino group. Among these glutamate-pyruvate transaminase (GPT) and glutamate-oxaloacetate transaminase (GOT) blood concentrations may be indicative of liver diseases and, therefore, quantitative analysis of GPT and GOT activities is very important in the diagnosis of liver diseases.

GPT and GOT are transaminases which catalyze transamination between an amino acid and an α-keto acid to produce another amino acid, as shown by the following reaction schemes (1) and (2).

$$\alpha\text{-Ketoglutarate} + \text{L-Alanine} \underset{}{\overset{GPT}{\rightleftarrows}} \text{Pyruvate} + \text{L-Glutamate} \quad (1)$$

$$\alpha\text{-Ketoglutarate} + \text{L-Aspartate} \underset{}{\overset{GOT}{\rightleftarrows}} \text{Oxaloacetate} + \text{L-Glutamate} \quad (2)$$

Enzyme assay may be classified into two methods; one is called an endpoint method for assaying an amount of substrate in which an enzyme-catalyzed reaction is quantitatively proceeded and after completion of the reaction, an amount of substrate or product changed is measured at the endpoint as a detectable species. The endpoint method thus involves a reaction system in which a detectable species, typically a dyestuff, is formed in an amount equivalent to the amount of substrate consumed in a fixed period of time, i.e., the substrate decreases with time to reach the endpoint of the enzyme reaction for a fixed period of time. Another method is called the kinetic or rate-determining method for assaying enzyme activity which comprises measuring a detectable change of a physical amount with time; in this case, it is not required that the reaction be completed, unlike the endpoint method. More specifically, in the kinetic method a catalytic reaction proceeds due to interaction between the enzyme contained in a liquid sample and a substrate, and the amount of the reaction product increases or decreases with time in a linear relationship between the product produced and time. These two methods are explained in *Method of Enzymatic Analysis*, Hans Ulrich Bergmeyer, vol. 2, pages 726–773 (1974), published by Academic Press, Inc., New York, referring to measurement of transaminase activity. According to the Reitman-Frankel method (which is the endpoint method described in *Amer. J. Clin. Pathol.*, vol. 28, page 56 (1956)), oxaloacetate produced after incubation for a fixed period of time is chemically converted into pyruvate; 2,4-dinitrophenylhydrazine is added to the pyruvate and the 2,4-dinitrophenylhydrazone formed is optically measured at 500 to 550 nm. On the other hand, according to the Karmen method (which is the kinetic or rate-determining method described in *J. Clin. Invest.*, vol. 34, page 131 (1955)) as illustrated below, enzyme reaction (1') is immediately coupled with enzyme reaction (2'). In reaction (2'), wherein a rate of decreasing absorption of coenzyme NADH is measured at 340 nm.

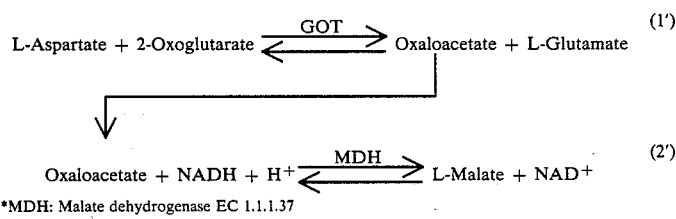

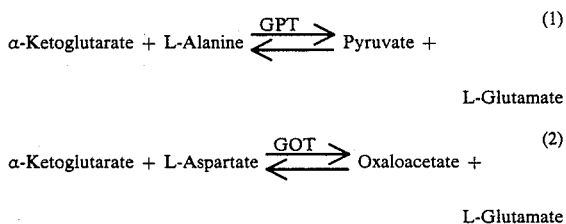

*MDH: Malate dehydrogenase EC 1.1.1.37

In the past, the activities of transaminases have been measured by a color reaction in which a diazo dye is coupled with the pyruvate or oxaloacetate formed according to equations (1) or (2) (Japanese Patent Application (OPI) 40191/76) (the term "OPI" as used herein refers to a published unexamined patent application). The reaction system involved in the Japanese Patent Application *supra* belongs to the aforesaid endpoint method similar to the Reitmean-Frankel method. As an embodiment of this prior art method, a multilayer analysis film wherein the sequential reactions described above are intended to be separately conducted in two adjacent reagent layers has been proposed. The object is to reach equilibrium of the enzyme reaction of the first stage prior to beginning the coupling reaction of the second stage by conducting the two reactions at a suitable interval. Thus, this method runs counter to current needs in the art that reaction time (time required for assay) should be shortened as much as possible and, further, the sensitivity thereof is far from satisfactory.

There has also been proposed a method for the quantitative measurement of the activity of various transaminases where pyruvate is formed directly as shown in equation (1) above or indirectly from oxaloacetate formed according to equation (2) by way of a reaction in which another enzyme may or may not be involved, whereafter hydrogen peroxide - formed from the pyruvate by pyruvate oxidase (POP) according to equation (3)-, a color indicator composition and a peroxidase form a dye, according to equation (5). Thus, the resultant color level may be measured colorimetrically (for example, see Japanese Patent Application (OPI) 13068/80).

The measurement system of the present invention is a kinetic or rate-determining method similar to the Karmen method, in which applying several steps of conventional, enzymatically coupled reactions described hereinafter to reaction (1) or (2), the product produced (pyruvate in reaction (1) and oxaloacetate in (2)) is immediately converted into a detectable chemical species (NADH or a dye) and increase or decrease of the detectable chemical species is measured with time. In the rate-determining method utilizing several steps of coupled reactions, the enzyme activity of GOT or GPT should be reflected on the detectable chemical species to be actually measured.

The principle of the transminase assay used in the present invention which is described in Japanese Patent Application (OPI) 13068/80 is shown below.

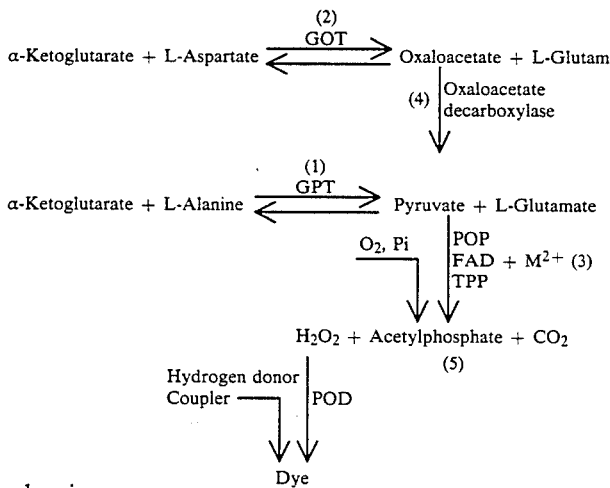

wherein:
GOT: Glutamate-oxaloacetate transaminase
GPT: Glutamate-pyruvate transaminase
Pi : Inorganic phosphoric acid
POP: Pyruvate oxidase
FAD: Flavin adenine dinucleotide
TPP: Thiamine pyrophosphoric acid
$M^{2+}$: Bivalent metal
POD: Peroxidase As is evident from the reaction schemes above, GOT enzyme reaction (2) is coupled with reactions (4), (3) and (5) in turn and, GPT enzyme reaction (1) is coupled with reactions (3) and (5) in turn. Namely, pyruvate formed according to the GPT-catalyzed reaction (1) or formed by GOT-catalyzed reaction (2) coupled with reaction (4) by the action of oxaloacetate decarboxylase, is converted into hydrogen peroxide according to POP-catalyzed reaction (3) which is further coupled with indicator enzyme reaction (5).

The POD enzyme reaction (5) where the thus produced hydrogen peroxide is a substrate, effects a coupling reaction between a hydrogen donor and a coupler to form a dye which is then subjected to a colorimetrical quantitative measurement.

In the aforesaid coupled reaction system of a kinetic method, it is important that the enzyme activity of GOT or GPT be reflected on the detectable species (dye) actually measured. In other words, an intermediate product should not accumulate but once it is formed, it should be immediately converted into a final product. For example, when a rate of reaction (3) is slower than that of reaction (4), reaction (3) cannot proceed but pyruvate which is the product of reaction (4) simply accumulates. This is fatal to the rate-determining method since the GOT activity is not reflected on the dye in reaction (5). Contrary to the rate-determining method, no fatal problem occurs with the endpoint method because the reaction finally reaches the endpoint anyhow; merely a longer time is required to complete the reaction.

As described above, GOT or GPT activity is assayed through a series of chemically coupled reactions which are conducted in an aqueous solution. However, precise control of the weight or volume of the components and troublesome handling of an aqueous solution are needed in order to perform these complicated reactions at high efficiency. In addition, the analysis procedures require a long time. Accordingly, this is not a satisfactory method for clinical assays in which both quickness and accuracy are needed.

The normal concentration of transaminase in healthy human blood is about 20 IU/1 at most, and the quantity of the substrate on which the enzymatic action of transaminase occurs during several tens of minutes for the measurement according to the method of the prior art is on the degree of $10^{-4}$ mole/l under optimum condition. In a method for the colorimetric measurement of such trace amounts of a substrate using a coupled enzyme reaction, it is required—to maintain the accuracy of the results and to shorten the time for the analysis procedure—that: (1) each reaction fully proceed; (2) the dye formed have high absorbance; (3) the dye remain stable until it is photometrically measured; and (4) the dye formed not be lost by migration or diffusion prior to measurement in the case of a colorimetrical measurement using a film for quantitative analysis.

It is known that various oxidase enzymes, e.g., lactate oxidase or cholesterol oxidase, can be incorporated in a reagent layer or a spreading layer (see U.S. Pat. Nos. 4,166,763 issued to Esders et al and U.S. Pat. No. 3,983,005). However, the methods disclosed in these patents relate to endpoint colorimetry in which a dye is formed in an amount equivalent to substrate in a fixed period of time-, i.e., the dye is measured at the endpoint of the reaction. In these methods, there is no reason to give consideration to a rate-determining step. It is thus sufficient, as taught in U.S. Pat. No. 4,166,763, that 500 U/m² of oxidase enzymes be present at maximum in a slide for the endpoint method. In view of these points, the present inventors have conducted extensive investigations and have found that the feed of oxygen, one of the substrates for the pyruvate oxidase, is a rate-determining step in the successive reaction system described above, and that the rate at which the hydrogen peroxide migrates from one layer of the multilayer film to another is much higher than that of migration rates of other substrates or products; the present invention has thus been accomplished.

SUMMARY OF THE INVENTION

It is an object of this invention to provide a multilayer analysis film in which each of constituents used for the quantitative analysis of transminase activity and designed to produce hydrogen peroxide is present in a specified layer.

Another object of the present invention is to provide a multilayer analysis film in which transaminase activity is assayed in a simple manner with high accuracy by coupling with a known POP reaction system.

A further object of the present invention is to provide a method for the quantitative analysis of transaminase in a coupled reaction system by a kinetic method.

A multilayer analysis film per this invention has a structure wherein a porous layer containing substrate of transaminase, a color indicator layer for detecting hydrogen peroxide and a transparent support are integrally laminated, in this order. The multilayer analysis film is characterized in that:
 (a) a pyruvate oxidase (hereafter often referred to as POP) is located in the analysis film where POP-catalyzed reaction (3) receives maximum exposure to oxygen in the air and therefore, POP is contained in the uppermost porous layer or an upper layer which is typically an enzyme layer located in contact with both the porous layer and the color indicator layer; and,
 (2) the impregnation amount of POP is from 1,000 to 100,000 U/m$^2$.

Figure 1:
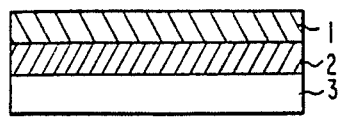
FIGS. 1 to 9 are enlarged sections showing various embodiments of multilayer analysis films of the present invention.
Figure 5:
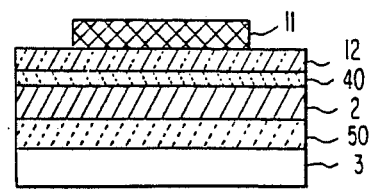

The numerals shown in the drawings have the following meanings:
 1 is a porous layer containing TA (transaminase) substrate - POP, 11 is a porous layer containing a TA substrate, 12 is a POP enzyme layer, 2 is a color indicator layer, 21 is a color indicator layer containing a mordant, 22 is a color indicator layer containing a mordant - TiO$_2$, 3 is a support, 40 is a light blocking layer containing TiO$_2$ and 50 is a mordanting layer.

PREFERRED EMBODIMENTS OF THE INVENTION

As shown principally in the Karmen method of a kinetic system, the reaction for detection generally called indicator reaction which is coupled with the enzyme-catalyzed reaction should proceed immediately. The reaction for detection should always possess a reaction rate that is at least the same as that of the enzyme catalytic reaction; otherwise, a linear relationship is not obtained between the amount of detectable species and time. Phrased another way, any rate-determining step for producing a detectable species can no way be involved in steps for the reaction for detection. Noting such characteristic of the kinetic method, the production of the dye as the detectable species at high efficiency which results in high detection sensitivity can be achieved by determining the location and amount of POP enzyme. This is, of course, based on the finding that reaction (3) is rate-determining and depends on a concentration of oxygen; therefore, POP is located in the analysis film where POP-catalyzed reaction (3) receives maximum exposure to oxygen in the air.

The multilayer analysis film per this invention has a structure wherein the porous layer containing a substrate of transaminase, a color indicator layer for detecting hydrogen peroxide and a transparent support are integrally laminated, in this order. The uppermost porous layer further contains POP, but POP need not always coexist with the substrate and may be contained in another layer (referred to as an enzyme layer) which comes into fluid contact (through a gas or a liquid) with the porous layer and is laminated on the color indicator layer. In the present specification the term "fluid contact" refers to zones which are associated with one another in a manner such that, under conditions of use, a fluid, whether liquid or gaseous, can pass from one to the other.

As described above, when POP is located in the uppermost layer or in an upper part of the multilayer analysis film, oxygen which is one of the substrates for POP can be more efficiently fed from the air, in addition to oxygen dissolved in a test solution (see equation(3)). As a result, in a POD enzyme reaction (see equation (5)) coupled with the reaction of equation (3), hydrogen peroxide which is a substrate of POD is sufficiently and rapidly produced.

The hydrogen peroxide thus formed has a large mobility from the porous layer into the color indicator layer due to its low molecular weight, when the porous layer and the color indicator layer are in a wet state by application of a test solution. Thus the hydrogen peroxide immediately diffuses, migrates into and reach he indicator layer where a color-forming reagent such as a coupler reacts therewith to give a colored product.

In the multilayer analysis film of the present invention, it is important that feeding of oxygen from the air determines the overall reaction rate of the reaction system as a whole. It is also important that hydrogen peroxide having the largest multilayer mobility play to rapidly move from the porous layer to the color indicator layer. Therefore, POP may be placed anywhere as long as it permits performance of these functions; however, it is generally placed in the upper porous layer containing the substrate of transaminase or in a layer adjacent thereto toward the support side. Since these layers come or substantially come into contact with air, the reaction of equation (3) proceeds rapidly.

The reaction product or hydrogen peroxide is colorless and therefore, begins migration under conditions undetectable colorimetrically and immediately reaches the indicator layer where a detectable colored product is then formed. Per the present invention, it is very important that the multilayer migrant be undetectable.

In the prior art described above, the possibility exists that a coloring reaction product under migration will be colorimetrically measured unless analysis is carried out after a relatively long period during which the migration of the colored reaction product in the reaction layer is completed and fixed to a detection layer, since the colored product migrates from the reaction layer to the detection layer at a low migration speed. On the contrary, there is no such possibility in the present invention in which the migrant is undetectable.

Transaminases whose activity may be measured according to the present invention are those which are specifically described in the classification No. 2.6.1 of Enzyme Nomenclature, 1972 edition, published by Elsevia Co. (1973) approved by International Union of Biochemistry, such as glutamic-oxaloacetic transaminase (GOT), glutamic-pyruvic transaminase (GPT), L-Aspartate: 2-oxoglutarate aminotransferase (EC 2.6.1.1), L-Alanine: 2-oxoglutarate aminotransferase (EC 2.6.1.2), Alanine-glyoxylate transaminase (EC 2.6.1.44) and β-Alanine transaminase (EC 2.6.1.18).

An indirect reaction in which pyruvate is produced may be one in which another enzymatic reaction as shown by equation (4) is concerned or may be a non-enzymatic chemical reaction. In any case, any process in which an enzymatic or chemical reaction is used in combination with a transaminase reaction to produce hydrogen peroxide as a final product from pyruvate may be used. Among them, measurement of GOT and GPT activities are most important diagnostically.

The substance which is a substrate for the transaminase is only required to have an amino group therein, and since the relationship between a substrate - enzyme couple is well known by those in the art, no detailed explanation will be given.

Transaminase is an enzyme which promotes transfer of the amino group in an amino acid to an α-keto acid. The substrate for transaminase includes the amino acid and α-keto acid.

POP used in the multilayer analysis film of the present invention is usually activated by a POP activator in order to accelerate the reaction. Examples of the POP activator include coenzymes, inorganic phosphates, bivalent metal ions and the like.

The POP activator is generally employed in an amount of $10^{-9}$ to $10^{-5}$ mole per unit of POP.

Typical coenzymes include flavin adenine dinucleotide, thiamine pyrophosphate, etc.; typical inorganic phosphates include primary and secondary sodium phosphates, primary and secondary potassium phosphates, etc.; and, typical bivalent metal ions include $Mg^{2+}$, $Mn^{2+}$, $Ca^{2+}$, $Co^{2+}$ and the like.

The porous layer used in the present invention may be fibrous or nonfibrous. As a porous fibrous material, a paper such as a filter paper, a synthetic paper, a nonwoven fabric and polyethylene pulp, and cloth such as natural or synthetic woven fabrics, especially plain fabrics, may be used. Specific examples of these materials are described in detail in Japanese Patent Application (OPI) 164356/80 (corresponding to U.S. Pat. No. 4,292,272). In addition, a membrane filter or beads such as glass, polymers, ceramics and a mixture thereof may be used as the porous, non-fibrous material. Specific examples of such materials are described in Japanese Patent Publication No. 21677/78 (corresponding to U.S. Pat. No. 3,992,158).

The pore size of the porous layer is within the range of from 0.05 to 300 μm, preferably 0.1 to 100 μm.

The degree of porosity of the porous layer is generally within the range of from 25 to 85%, preferably 40 to 85%.

The porous layer has a thickness generally in the range of from 50 to 500 μm, preferably 100 to 400 μm.

The porous layer can also function as a definite area-spreading layer so that the amount of a liquid sample retained in the porous layer is determined by the definite area and the thus determined amount of the liquid sample is transferred to a layer therebeneath in the same amount and area as in the porous layer.

Such porous materials are impregnated with a solution containing a transaminase substrate or a mixture of a transaminase substrate and POP to obtain a porous layer. In the case that the porous layer contains only a transaminase substrate, POP may be coated to form a POP enzyme layer (an enzyme layer) adjacent the porous layer. The POP enzyme layer has generally a thickness of from 1 to 100 μm, preferably 5 to 50 μm.

The color indicator layer for the detection of hydrogen peroxide preferably has a thickness of 1 μm to 100 μm and, preferably 5 to 50 μm comprises a composition prepared by dispersion of a coupler and a hydrogen donor into a known hydrophilic binder such as gelatin, polyvinyl alcohol, polyvinyl pyrrolidone, agarose, sodium polyvinyl benzenesulfonate and the like.

Once an analyte is determined, the impregnation amount for components is correspondingly determined but generally in a range set forth below.

|  | General Range | Preferred Range |
| --- | --- | --- |
| Substrate (g/m$^2$) | 0.5–500 | 1–150 |
| Coupler (g/m$^2$) | 0.01–5 | 0.1–3 |
| Hydrogen Donor (g/m$^2$) | 0.01–5 | 0.1–3 |
| POP (U/m$^2$) | 1,000–100,000 | 1,000–50,000 |
| Oxaloacetate Decarboxylase (U/m$^2$) | 500–100,000 | 1,000–50,000 |
| Coenzyme (g/m$^2$) | 0.01–10,000 | 0.1–5,000 |

Preferably, a cationic dye forming system is selected as a color indicator system for the detection of hydrogen peroxide and most preferably, 4-aminoantipyrine or N,N-disubstituted-p-phenylenediamine as a hydrogen donor and a combination of an N,N-disubstituted-aniline derivative and an anionic polymer as a coupler are used. Such a system has many advantages, that is, efficiency of conversion into the colored reaction product is high, the cationic dye produced has high absorbance, the colored reaction product (dye) can be efficiently fixed and, thus, the sensitivity of measurement is remarkably high.

As the support, known water impermeable transparent film materials such as polyethylene terephthalate, cellulose esters (cellulose diacetate, cellulose triacetate, cellulose acetate propionate and the like), polycarbonate, polymethyl methacrylate or a glass plate having a thickness of about 50 μm to about 2 mm are conveniently used.

In addition, a transparent support as described above into which a pigment such as carbon black, titanium oxide, or copper phthalocyanine is dispersed or an opaque support such as a stripping paper may also be used. In this case, upon completion of the assay, the support is removed prior to the subsequent colorimetric measurement.

Figure 2:
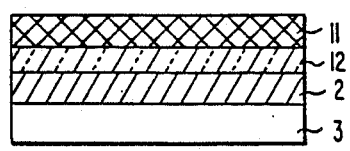
Figure 6:
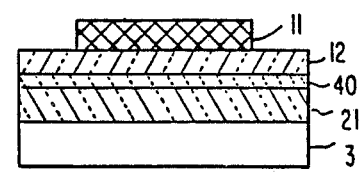
Figure 3:
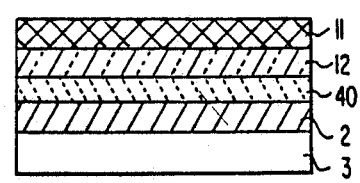
Figure 7:
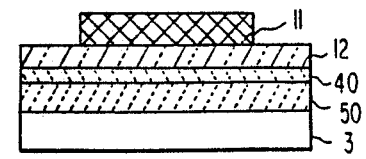
Figure 4:
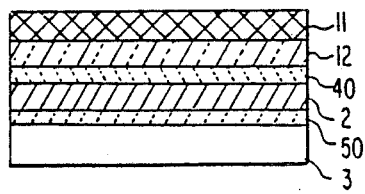
Figure 8:
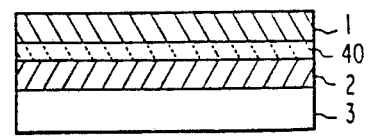
Figure 9:
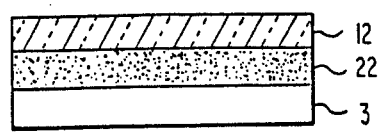

In addition to the fundamental structure described above (see FIGS. 1 and 2), the multilayer analysis film of the present invention may have other various structures or functional auxiliary layers such as a color masking, or light blocking or light reflecting, adherent and mordanting layers (1 to 50 μm, preferably 1 to 30 μm) which may be formed in a conventional manner. Representative embodiments of this invention having such auxiliary layers are shown in FIGS. 3 to 9.

The layer thickness of the radiation-blocking or light-reflecting layer is generally in the range of from 1 to 50 μm, preferably 2 to 10 μm.

The multilayer analysis film of the present invention may be prepared by, for example, bringing one layer into intimate contact with another layer, if necessary or desired, after wetting the surface of the layers with water or an aqueous solution of a surface active agent, and passing the layers through between pressure rolls to form a laminate.

Analytical operation can generally be conducted as follows: A calibration curve for the multilayer analysis film of the present invention is generated by spotting commercially available calibrator solutions containing from 0 to 800 IU transaminase/1 on the film, incubating the film for about 30 seconds to about 20 minutes at 37° C., and thereafter detecting the color density produced in the color indicator layer by spectrophotometry through a transparent support. A liquid sample, containing an unknown transaminase level, is then spotted on separate but identical samples of the film and the transaminase level is determined on each by use of the previously generated calibration curve.

In general, the total time of analysis is between about 3 to about 30 minutes.

The multilayer analysis film thus prepared of the invention has the following advantages:

(1) The time for the whole analysis is shortened because the feed of oxygen (i.e., exposure to the air) which is a rate-determining step of the reaction is carried out at a high efficiency.

(2) Remarkably high sensitivity is achieved, because hydrogen peroxide, which is a chemical species colorimetrically undetectable, is used as a primary migrant, i.e., the process from the beginning to the oxidase reaction is carried out in an upper layer where the distance of diffusion and migration is short, and the color-forming reaction is carried out in an indicator layer adjacent the transparent support having a high detection efficiency.

(3) High accuracy is obtained because the transaminase reaction product is converted into a detectable dye at a high efficiency.

(4) As a consequence of the above advantages, the range in which the transaminase activity may be quantitatively measured is expanded.

In the examples given below, layers were dried at 15° C. for 30 minutes and at 40° C. for 30 minutes, unless otherwise indicated.

EXAMPLE 1

On a colorless, transparent polyethylene terephthalate (PET) film (a photographic support) was applied a dye fixing layer having the following composition to give a dry thickness of 10 μm.

Composition of the coating liquid for the dye fixing layer:

| | |
|---|---|
| Gelatin | 5.0 g |
| Potassium polystyrene-4-sulfonate (molecular weight 340,000) | 2.5 g |
| Surfactant 10 G ® (a nonionic surface active agent produced by Olin Chemicals Co., p-octylphenoxypolyethoxyethanol) | 0.50 g |
| Bis(vinylsulfonylmethyl) ether | 0.20 g |
| Glycerin | 1 g |
| Water | 100 ml |

On the resulting dye fixing layer there was coated a coating liquid having the following composition to give a color indicator layer having a dry thickness of 15 μm. Composition of the coating liquid for the color indicator layer:

| | |
|---|---|
| N,N—(bis(β-hydroxyethyl)-m-toluidine | 0.20 g |
| 4-Aminoantipyrine hydrochloride | 0.24 g |
| Gelatin | 15 g |
| POD(EC. 1.11.1.7; hereafter the same) | 7500 units |
| Surfactant 10 G ® | 0.50 g |
| Bis(vinylsulfonylmethyl) ether | 0.38 g |
| Water | 100 ml |

On the resulting layer there was then coated a coating liquid having the following composition to provide a light blocking layer having a dry thickness of 7 μm.

Composition of the coating liquid for the light blocking layer:

| | |
|---|---|
| Finely divided TiO$_2$ powder | 19.5 g |
| Gelatin | 6.8 g |
| Sodium dioctyl sulfosuccinate | 1.0 g |
| Water | 87 g |

Onto the resulting light blocking layer these was coated a coating liquid having the following composition to obtain a pyruvate oxidase layer (POP layer) having a dry thickness of 10 μm.

COMPOSITION OF THE COATING LIQUID FOR THE POP LAYER

| | |
|---|---|
| Gelatin | 10 g |
| POP(EC. 1.2.3.3; hereafter the same) | 5000 units |
| FAD | 4.1 mg |
| TPP | 92 mg |
| MgCl$_2$ | 47 mg |
| Surfactant 10 G ® | 0.50 g |
| Water | 100 ml |

A solution of a GPT substrate having the following composition was then prepared.

| | |
|---|---|
| Sodium α-ketoglutarate | 3.8 g |
| L-Alanine | 35.6 g |
| Disodium hydrogen phosphate 12H$_2$O | 10.9 g |
| Sodium dihydrogen phosphate | 3 g |
| Polyacrylamide | 2 g |
| Surfactant 10 G ® | 2 g |
| Water | 400 ml |

A filter paper for electrophoresis having a smooth surface (400 μm thick) was dipped in to the resulting GPT substrate solution and was passed between silicon rubber rolls spaced at intervals of 500 μm to be uniformly impregnated with the solution. Then, the filter paper was spontaneously dried on the surface of a flat glass plate.

The filter paper impregnated with the GPT substrate solution was used as a porous layer containing a TA substrate composition. The porous layer was pressed on the multilayer coated PET film previously wetted with an aqueous solution of Surfactant 10 G (2% V/V aqueous solution) and then dried to fix the same thereto. Thus, a multilayer analysis film (A) for the quantitative analysis of GPT was obtained.

REFERENCE EXAMPLE 1

In the multilayer analysis film for the quantitative analysis of GPT (A), instead of application of the POP layer, a coating liquid having the following composition prepared by the addition of POP to the color-forming reagent layer was formed to have a dry thickness of 18 μm. In this case, the amount of POP was 1.5 times that in Example 1 and, therefore, the amounts of the activator of pyruvate oxidase or FAD, TPP and $MgCl_2$ were increased in proportion to that of POP. However, the amount of POD was the same as in Example 1 because the color to be finally measured is formed by the enzymatic reaction of POD with $H_2O_2$ converted by the enzymatic reaction of POP.

Composition of the coating liquid for the POP-coloring reagent layer:

| | |
|---|---|
| N,N—Bis(β-hydroxyethyl)-m-toluidine | 0.20 g |
| 4-Aminoantipyrine hydrochloride | 0.24 g |
| Gelatin | 15 g |
| POD | 7500 units |
| POP | 8000 units |
| FAD | 6.2 mg |
| TPP | 0.138 g |
| $MgCl_2$ | 70.7 mg |
| Surfactant 10 G ® | 0.50 g |
| Bis(vinylsulfonylmethyl) ether | 0.38 g |
| Water | 100 ml |

On the resulting multilayer coated film, the filter paper impregnated with the GPT substrate composition for the above-mentioned porous layer containing the TA substrate composition was pressed while wet to obtain a multilayer analysis film (B) for the quantitative analysis of GPT.

Analysis films (A) and (B) thus obtained were cut to form specimens 0.5 cm². Commercially available control serums to which various amounts of GPT enzyme were added were spotted on the TA substrate layer of the specimen.

Test Method:

The films described above were placed on a plastic slide frame to prevent water evaporation and were incubated at 37° C. Incubation was performed for 20 mins., in which optical density was measured at 30 second intervals. Data obtained 10 mins. after the measurement were plotted (FIG. 10).

Color density changes with the passage of time were measured on a reflection spectrophotometer.

Figure 10:
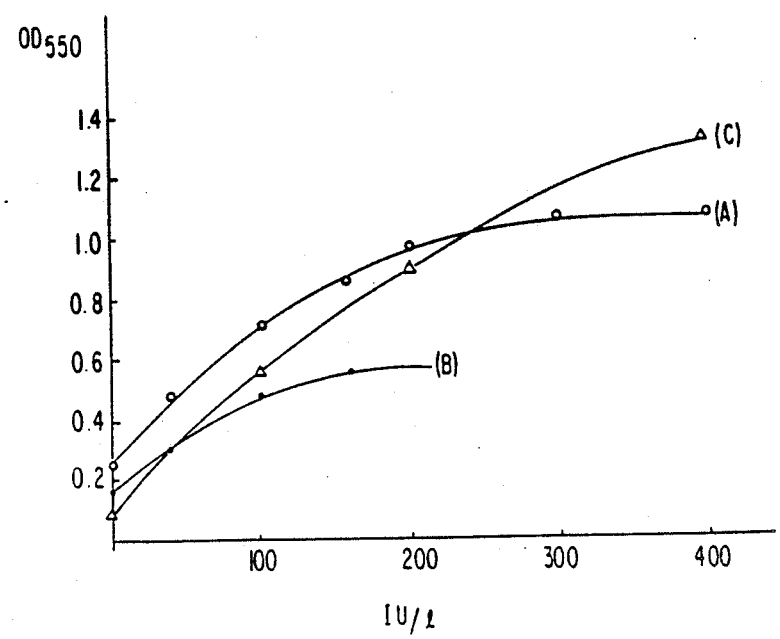
FIG. 10 is a graph showing the color densities measured 10 minutes after incubation of analysis films for GOT analysis (A), (B) and (C) obtained according to Example 1, Reference Example 1 and Example 2, respectively, wherein enzyme activities (IU/1) are shown on the abscissa and optical densities at 550 nm are shown on the ordinate.

The results obtained are shown in FIG. 10.

As seen from FIG. 10, the GPT analysis film (B) according to the prior art, although containing 1.5 times the amount of POP, is inferior to GPT analysis film (A) according to the present invention in color density and the analysis range of film (B) is narrower than that of film (A).

REFERENCE EXAMPLE 2

The following procedure was conducted to obtain GPT analysis film (B') in a manner similar to Reference Example 1.

(1) The amounts of FAD, TPP, $MgCl_2$ and the POP activator were the same as in Example 1, respectively.

(2) 3400 Units of POP was added to the coloring reagent layer as such an amount of POP was in proportion to that of the POP activator.

(3) Other conditions were the same as those in Reference Example 1.

Thus, the same amount of POP was used in all Examples of analysis film (A) according to the present invention and comparative analysis films (B) and (B').

Coloration speed was observed with respect to comparative analysis films (B) and (B').

Samples—each 20 μl of a $10^{-3}$ M pyruvate aqueous solution—were spotted on analysis films (B) and (B') and coloration speed was measured using a reflection spectrophotometer in a manner similar to Reference Example 1. The color density of analysis film (B') was only 80% that of analysis film (B).

Similar results were obtained when the control serum contained 140 IU/l of GPT.

From the results of Example 1 and Reference Examples 1 and 2, it can be seen that analysis film (A) according to the present invention, even if the amount of POP used is two thirds of that of analysis film (B), gave much higher color density than analysis film (B), and had a broader range of quantitative analysis and, accordingly, the above advantages of the present invention will be further increased when the same amount of POP activator as that of the comparative films is used.

EXAMPLE 2

Instead of the POP substrate layer of GPT analysis film (A) described in Example 1, an intermediate layer comprising only gelatin was coated to give a membrane of a 5 μm dry thickness.

Then, a filter paper for electrophoresis having a smooth surface (400 μm thick) was cut to 0.5 cm² and was then wet and pressed (laminated) on the multilayer coated film in a manner similar to Example 1.

POP and coenzymes thereof were added to the GPT substrate composition of Example 1 to prepare a solution of GPT substrate-POP composition having the following composition.

SOLUTION OF GPT SUBSTRATE-POP COMPOSITION

| | |
|---|---|
| Sodium α-ketoglutarate | 3.8 g |
| L-Alanine | 35.6 g |
| Disodium hydrogen phosphate $12H_2O$ | 10.9 g |
| Sodium dihydrogen phosphate $2H_2O$ | 3 g |
| POP | 40,000 units |
| FAD | 0.033 g |
| TPP | 0.74 g |
| $MgCl_2$ | 0.37 g |
| Gelatin | 2 g |
| Surfactant 10 G ® | 5 g |
| Water | 400 ml |

The solution of GPT substrate-POP composition cooled to 0° C. (20 μl) was spotted on the filter paper adhered to the multilayer coated film described above and was then subjected to rapid freeze drying in vacuo to obtain analysis film for GPT analysis (C).

A performance test of the analysis film for GPT analysis (C) was conducted similar to Example 1. The results are shown in FIG. 10.

EXAMPLE 3

In the analysis film for GPT analysis (C) described in Example 2, instead of the light blocking layer, a membrane filter cut in the form of a circle having a diameter of 9 mm (Fuji Microfilter ® (mean pore size 5 μm) FM-500 produced by Fuji Photo Film Co.) was adhered by wet pressing similar to Example 2.

Then, 10 μl of the GPT-POP composition solution described in Example 2 was spotted thereon and the composite freeze dried to obtain an analysis film for GPT analysis (D).

By a method similar to Example 1, 10 μl of a commercially available control serum having a GPT activity of 105 IU/dl was spotted thereon and the composite incubated at 37° C. for 10 mins. The GPT activity was monitored by the coloration speed with the passage of time. The coloration increased linearly for more than 20 minutes and the speed was about three times that of the analysis film for GPT analysis (C).

EXAMPLE 4

A filter paper for electrophoresis (500 μm thick) was used instead of the membrane filter of Example 3 and was impregnated with the following GOT substrate-enzyme solution and dried per the method of Example 1, then wet pressed to adhere the same to the multilayer coated film described in Example 3.

| GOT substrate-enzyme solution: | |
|---|---|
| L-Aspartic acid | 50 g |
| Sodium α-ketoglutarate | 3.0 g |
| Disodium hydrogen phosphate 12H$_2$O | 10.9 g |
| Sodium dihydrogen phosphate 2H$_2$O | 3.0 g |
| POP | 40,000 units |
| Oxalaceate decarboxylase (EC.4.1.1.3) | 50,000 units |
| FAD | 0.033 g |
| TPP | 0.74 g |
| MgCl$_2$ | 1 g |
| Triton X-100 (a nonionic surface active agent produced by Rohm and Haas Co., Ltd., p-octylphenoxypolyethoxy ethanol) | 5 g |
| Water | 400 ml |

The resulting analysis film for GOT analysis was cut to yield a specimen 0.8 cm square which was then inserted in a plastic slide frame designed for a dry analysis film and was preheated for 2 minutes at 37° C.

Samples each 30 μl—of GOT solutions in physiological saline at concentrations of 53, 104, 210 and 401 IU/l respectively, were spotted on the specimen, the opening spotted was sealed with an adhesive tape and then the specimen was incubated for 10 minutes at 37° C. and the color density measured using a reflection spectrophotometer. The results are given in Table 1.

TABLE 1

| GOT Activity (IU/l) | 53 | 104 | 210 | 401 |
|---|---|---|---|---|
| Reflection Density | 0.75 | 1.14 | 1.42 | 1.68 |

GOT activity was measured with high sensitiveness over the broad range of concentrations using the analysis film for GOT analysis of the present invention.

While the invention has been described in detail and with reference to specific embodiments thereof, it will be apparent to one skilled in the art that various changes and modifications can be made therein without departing from the spirit and scope thereof.

What is claimed is:

1. A multilayer analysis film for transaminase analysis in a coupled reaction system which has formation of pyruvate by a kinetic method as part of the coupled reaction system, containing constituents for the quantitative analysis of transaminase, said film comprising a transanimase substrate, a pyruvate oxidase, an activator for the pyruvate oxidase and a color indicator for the detection of hydrogen peroxide, wherein a porous layer containing the transaminase substrate, a color indicator layer for the detection of hydrogen peroxide, and a transparent support are integrally laminated in this order, and the pyruvate oxidase and the activator for the pyruvate oxidase are contained in the porous layer or in an enzyme layer which is in contact with both the porous layer and the indicator layer, wherein the impregnation amount of the pyruvate oxidase is from about 4,698 to about 34,707 U/m$^2$ and an amount of a detectable species produced in said coupled reaction system by a kinetic method has a specific relation with time.

2. The multilayer analysis film for transaminase analysis as defined in claim 1 wherein said porous layer or said enzyme layer contains oxalacetic acid and decarboxylase.

3. The multilayer analysis film for transaminase analysis as defined in claim 1 or 2 wherein said porous layer is a porous spreading layer.

4. The multilayer analysis film for transaminase analysis as defined in claim 1 or 2 wherein said porous layer has a definite area which determines the amount of a sample liquid and the transfer thereof to a layer therebeneath through the definite area.

5. The multilayer analysis film for transaminase analysis as defined in claim 1 wherein said activator for the pyruvate oxidase comprises a coenzyme, a source of an inorganic phosphoric acid and a bivalent metal.

6. The multilayer analysis film for transaminase analysis as defined in claim 5 wherein said coenzyme is flavin adenine dinucleotide and thiamine pyrophosphate.

7. The multilayer analysis film for transaminase analysis as defined in claim 1 wherein, of all components present, said hydrogen peroxide, once formed, has the highest multilayer mobility.

8. A method for the quantitative analysis of transaminase in a coupled reaction system which has formation of pyruvate by a kinetic method as part of the coupled reaction system, comprising the steps of:

(A) applying a liquid sample to a multilayer analysis film for transaminase analysis, containing constituents for the quantitative analysis of transaminase, said film comprising transaminase substrate, a pyruvate oxidase, an activator for the pyruvate oxidase and a color indicator for the detection of hydrogen peroxide, wherein a porous layer containing the transaminase substrate, a color indicator layer for the detection of hydrogen peroxide, and a transparent support are integrally laminated in this order, and the pyruvate oxidase and the activator for the pyruvate oxidase are contained in the porous layer or in an enzyme layer which is in contact with both the porous layer and the indicator layer, wherein the impregnation amount of the pyruvate oxidase is from about 4,698 to about 34,707 U/m² and an amount of detectable species produced in said coupled reaction system by a kinetic method has a specific relation with time; and (B) detecting color density in the indicator layer over the course of time so as to measure transaminase activity.

9. The method for the quantitative analysis of transaminase as defined in claim 8 wherein said porous layer or said enzyme layer contains oxalacetate and a decarboxylase.

10. The method for the quantitative analysis of transaminase as defined in claim 8 wherein said porous layer is a porous spreading layer.

11. The method for the quantitative analysis of transaminase as defined in claim 8 wherein said porous layer has a definite area which determines the amount of a sample liquid and the transfer thereof to a layer therebeneath through the definite area.

12. The method for the quantitative analysis of transaminase as defined in claim 8 wherein said activator for the pyruvate oxidase comprises a coenzyme, a source of an inorganic phosphoric acid and a bivalent metal.

13. The method for the quantitative analysis of transaminase as defined in claim 12 wherein said coenzyme is flavin adenine dinucleotide and thiamine pyrophosphate.

14. The method for the quantitative analysis of transaminase as defined in claim 8 wherein, of all components present, hydrogen peroxide, once formed, has the highest multilayer mobility, whereby the rate-determining step of the analysis is the step of converting pyruvate into hydrogen peroxide which is exposed to oxygen.

15. The method for the quantitative analysis of transaminase as defined in claim 8 wherein said detectable species is a dye.

* * * * *

UNITED STATES PATENT AND TRADEMARK OFFICE
CERTIFICATE OF CORRECTION

PATENT NO. : 4,897,347

DATED : January 30, 1990

INVENTOR(S) : HARUMI KATSUYAMA ET AL

It is certified that error appears in the above-identified patent and that said Letters Patent is hereby corrected as shown below:

On the cover page, under "[75] Inventors", the name of the second named inventor is Yoshikazu Amano.

Signed and Sealed this

Twentieth Day of August, 1991

*Attest:*

HARRY F. MANBECK, JR.

*Attesting Officer*         *Commissioner of Patents and Trademarks*